US008729034B2

(12) United States Patent
Kabir et al.

(10) Patent No.: US 8,729,034 B2
(45) Date of Patent: May 20, 2014

(54) PHARMACEUTICAL COMPOSITION HAVING VIRUCIDAL AND SPERMICIDAL ACTIVITY

(75) Inventors: Syed Nazrul Kabir, West Bengal (IN); Heramba Nanda Ray, West Bengal (IN); Bikash C. Pal, West Bengal (IN); Debashis Mitra, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 963 days.

(21) Appl. No.: 12/154,847

(22) Filed: May 27, 2008

(65) Prior Publication Data
US 2008/0300197 A1  Dec. 4, 2008

(30) Foreign Application Priority Data
Jun. 1, 2007 (IN) .......................... 1179/DEL/2007

(51) Int. Cl.
*A61K 31/704* (2006.01)
(52) U.S. Cl.
USPC .......................................... 514/33; 536/18.1
(58) Field of Classification Search
USPC .......................................... 514/33; 536/18.1
See application file for complete search history.

(56) References Cited

U.S. PATENT DOCUMENTS

2005/0148561 A1*  7/2005  Wild et al. .................... 514/171

OTHER PUBLICATIONS

Definition of prevent, WordNet, http://wordnet.princeton.edu/, accessed online on Nov. 14, 2007.*
Definition of derivative, Oxford English Dictionary, http://www.oed.com/, accessed online on Jan. 11, 2011.*
Definition of analog, Oxford English Dictionary, http://www.oed.com/, accessed online on Jan. 11, 2011.*
Pakrashi et al. Contraception, 1991, 43(5), p. 475-483.*
Jassim et al. Journal of Applied Microbiology, 2003, 95, p. 412-427.*

* cited by examiner

*Primary Examiner* — Shaojia Anna Jiang
*Assistant Examiner* — Jonathan S Lau
(74) *Attorney, Agent, or Firm* — Ladas & Parry LLP

(57) ABSTRACT

Acaciaside-B (Ac-B) has emerged as a prospective candidate molecule for prevention of HIV infection along with potential for use as/in vaginal contraceptive/formulation. It possesses anti-HIV property at a tolerably low concentration, is non-mutagenic and does not harm the niche of *Lactobacilli*. Thus Ac-B appears to be a superior ingredient for formulations of a chemical barrier against HIV-1 infection wherein its spermicidal property is superfluous.

25 Claims, No Drawings

PHARMACEUTICAL COMPOSITION HAVING VIRUCIDAL AND SPERMICIDAL ACTIVITY

FIELD OF INVENTION

The present invention relates to a pharmaceutical composition having virucidal and spermicidal activity. More particularly, the present invention relates to Acaciaside-B [Ac-B] and one of its co-isolate which is enriched with Acaciaside-B (Ac-B-en-frn), to be used as a prophylactic contraceptive for HIV infection/AIDS. The present invention further relates to the use of Ac-B and/or Ac-B-en-frn in mixture with other natural or synthetic substances in the field of drugs and pharmaceuticals, for preparing formulations/methodology/devices for protection against human immunodeficiency virus (HIV-1) infection through invasive sexual contacts and/or control of unwanted pregnancy. The present invention also relates to the use of the seeds of Acacia auriculiformis as raw materials for isolation of Ac-B to provide an active principle for preparation of over the counter (OTC) available self-administrable, prophylactic, vaginal formulation/contraceptive with anti-HIV hallmark.

BACKGROUND OF THE INVENTION AND DESCRIPTION OF PRIOR ART

Presently available spermicidal contraceptives contain ingredients including the neutral surfactants isononyl-phenyl-polyoxyethylene (9) ether or Nonoxynol-9 (N-9), p-menthanyl-phenyl-polyoxyethylene (8,8) ether or menfegol, isooctyl-phenyl-polyoxy-ethylene (9) ether or Octoxynol-9 (0-9) [K. Furuse, et al. J Pharmacobiodyn. 6: 359, 1983; G A Digenis, et al. Pharm Dev Technol.; 4: 421, 1999], etc. Of these, the most commonly used spermicidal contraceptive in the United Kingdom and the United States is N-9 [OTC Panel. Federal Register.; 45: 1980, 82014; E. Chantler. Brit Fam Plann.; 17, 118, 1992]. Other preparations/molecules under different phases of investigation are: Oxovanadium (IV) complexes of 1,10-Phenanthroline, 2,2'-Bipyridyl, 5'-Bromo-2'-Hydroxyacetophenone and derivatives [G A Digenis, et al. Pharm Dev Technol.: 4, 1999, 421]; Aryl Phosphate Derivative of Bromo-Methoxy Zidovudine (Compound WHI-07) [O. J D'Cruz., et al, Biology of Reproduction: 62, 2000, 37]; Lipophilic Vaginal Contraceptive Gel-Microemulsion, GM-144 [O J D'Cruz, et al. AAPS Pharm Sci Tech.; 2, article 5, 2001] and sodium nimidinate, the spermicidal agent of neem oil [DE Champagne, et al; Phytochemistry, 31, 377, 1992]. N-9 is being used at concentrations of 2% to 6% in creams and gels, 12% in foams, and as high as 18% in condom lubricants and 28% in vaginal contraceptive film. Frequent use of N-9 as a vaginal contraceptive/microbicide has been associated with an increased risk of vaginal or cervical infection, irritation, or ulceration [M L Rekart. J Acquir Immune Defic Syndr.; 5: 425, 1992, R E Roddy, et al. Int J STD HIV.; 4: 165, 1993, S S Weir, et al. Genitourin Med.; 71: 78, 1995]. In addition, it alters vaginal niche of bacteria or microflora, specially Lactobacilli and lead to an increased risk of opportunistic infections [T M Hooton, et al. JAMA.; 265: 64, 1991; M K Stafford, et al. J Acquir Immune Defic Syndr Hum Retrovirol.; 17: 327, 1998; I J Rosenstein, et al. J Infect Dis.; 177, 1386, 1998]. Such infections are known to enhance the susceptibility of the ectocervical epithelium and the endocervical mucosa to sexually transmitted pathogens including human immunodeficiency virus, type 1 (HIV-1) infection [J Kreiss, et al. JAMA.; 268, 477, 1992; M H Augenbraun, et al. Infect Dis Clin North Am.; 8: 439, 1994; EG Raymond, et al. Obstetrics & Gynecology.; 103, 430, 2004]. Frequent use of spermicidal vaginal foaming tablets containing menfegol is also associated with a high incidence of genital lesions [J Goeman, et al. J Infect Dis. 171, 1611, 1995]. Moreover, N-9 is composed of multiple oligomers that vary in ethyleneoxyde chain length and in biological performance [P. T. Fowler, et al AAPS Pharm Sci Tech 2003; 4(3) Article 30; B Walter, et al. Pharm Res, 1991; 8:409].

Thus, in short Nonoxynol-9 (N-9), the effective spermicidal molecule used widely in vaginal contraceptive formulations has been shown to render the user susceptible to STDs, including AIDS. The WHO has cautioned that N-9 containing formulations should not be used by those at risk of acquiring HIV infection.

Since heterosexual transmission of HIV-1 is the predominant mode of the epidemic spread of acquired immunodeficiency syndrome (AIDS), there is a pressing need to expedite research to get a safe, effective vaginal spermicidal product lacking strong toxicity and which may offer significant clinical advantage over the currently available medications in the market. A recent statement from the Medical Advisory Panel of the IPPF recommends that N-9 should be used only in combination with a mechanical barrier method and that condoms pre-lubricated with N-9 have no added advantage in contraceptive efficacy and should no longer be distributed to women at high risk of HIV/AIDS [IPPF Medical Bulletin, 37, 1, 2003].

India is one of the 12 mega-diversity countries in the world with a vital stake in conservation and sustainable utilization of its biodiversity resources. It is rich in vegetation of medicinal plants. One of such plants, Acacia auriculiformis (English: Earleaf Acacia, and Akashmoni/Sonajhuri in Bengali and Hindi), is a loose, rounded, evergreen, roadside or wild tree. The tree is also available in other parts of the world. The use of extracts from seeds of the tree is reported from time to time. The major components of the extracts are saponins of different kinds.

Herbal saponins are in use since the early age of human civilization specially for making toiletries. Some other medicinal properties of the saponins are also noted by different workers. Acaciaside-A and Ac-B, two acylated bisglycoside saponins originally isolated from the seeds of Acacia auriculiformis (B C Pal, et al. Indian Patent No. 186738] are known to have anti-helminthic activity [N K Ghosh, et al. J Helminthol. 70, 171, 1996]. Mandal et al. [Fitoterapia, 76, 462, 2005] reported that complete inhibition of conidial germination of Aspergillus ochraceous and Curvularia lunata was recorded at 300 μg/ml or less; whereas 700 μg/ml or higher concentrations of the mixture was required to inhibit the growth of Bacillus megaterium, Salmonella typhimurium and Pseudomonas aeruginosa. The conjugated unsaturated diene system of the saponins is likely to be involved in producing their damaging effect, probably by generation of free radicals that induce membrane damage through peroxidation [S P Sinha Babu, et al. Jpn J Pharmacolm. 75, 451, 1997; B Nandi, et al. Phytother Res., 18, 191. 2004]. Some other investigations suggest that the plant may contain active antimutagenic and chemopreventive agents [K. Kaur, et al Willd. Ex Del. Drug Chem Toxicol.; 25, 39, 2002] and antifilarial effect [M, Ghosh, et al Indian J Exp Biol. 31, 604, 1993; S B Mahato Adv Exp Med Biol. 404, 173, 1996]. A mixture of Acaciaside-A and Ac-B was reported to kill in vitro 97% microfilaria of Setaria cervi in 100 min at 4 mg/ml concentration and 100% of adults in 35 min. Farnsworth et al. reported that the majority of triterpine saponins, obtained from the plants, possess spermicidal properties [Research frontiers in fertility regulation 2, 1, 1982]. Setty et al reported that saponins, isolated from Indian medicinal plants, may act as potential spermicides [B S Setty, et al. Contraception 14: 571, 1976]. A series of bioactive triterpenoid saponins were characterized by a stringent structure-activity and were reported to be potent and selective inhibitors of human immunodeficiency virus type 1 (HIV-1) replication [Yang X W; et al. *J Nat Prod.* 1999: 62(11):1510-3].

A mixture of two analogous triterpenoid glycosides, Acaciaside-A and Ac-B, isolated from the seeds of *Acacia auriculiformis*, was reported to possess strong in vitro spermicidal property on human spermatozoa [A, Pakrashi, et al., Contraception 43: 475, 1991]. But a serious disadvantage of considering the mixture for formulation is that the MEC in humans is much higher (350 μg/ml) than that of pure Ac-B (125 μg/ml) [H Ray, et al., Unpublished observation]. Moreover, one of its major constituents (i.e. Acaciaside-A) is a mutagen.

The most intriguing aspect of Ac-B, however, is that its spermicidal effects involve damage of lipid molecules of the cell membrane [H Ray, et al., Unpublished Observation]. HIV requires intact lipid rafts, highly specialized sub-regions in cell membranes, for entry into cells and budding of fully infectious particles. By virtue of its lipid dispersing effects, Ac-B is likely to disrupt the lipid rafts as well as the lipid molecules of viral envelop and therefore, theoretically appears to be a likely prophylactic candidate for HIV infection.

OBJECTS OF THE INVENTION

The main objective of the present invention is thus to provide a pharmaceutical having virucidal property, which is capable of acting as a chemical barrier against HIV-1 infection (AIDS) along with a superfluous spermicidal property.

Another object of the present invention is to provide a prophylactic formulation/contraceptive that would provide a convenient, readily available method of self protection against AIDS and/or unwanted pregnancy.

Another objective of the present invention is to provide a naturally occurring molecule to be used as a chemical barrier against HIV-1 infection during invasive sexual interaction.

Another objective of the present invention is to provide an active principle for protection against other retroviruses.

SUMMARY OF THE INVENTION

The present invention provides a novel active principle of plant origin i.e. Acaciaside-B, which is non-mutagenic and/or Ac-B-en-frn, whose mutagenic potential is yet to be explored, that possess virucidal and spermicidal properties, and may be useful as an active principle for the preparation of OTC formulations, available as emergency protection against HIV-1 infection during heterosexual invasive contact and/or vaginal contraceptive, wherein the said composition comprising the therapeutically effective amount of Ac-B, or its derivatives, or analogues, or pharmaceutically acceptable enriched mixture with other inert and/or safe materials, thereof obtained from the extract of the seeds of *Acacia auriculiformis* for preparation of chemical barrier against HIV infection during heterosexual interaction or as OTC available vaginal formulation/contraceptive with prophylactic action.

The in vitro dosage for the said composition for the virucidal activity is ≥1.0 μg/ml and for spermicidal activity is 125 μg/ml for human sperms wherein the in vivo contraceptive dosage would increase as per requirement (e.g. 25 mg/ml KY-jelly for rabbit). Ac-B is water soluble and can be dissolved or dispersed in a number of carriers. For example, it may be formulated for "stand alone usage" in forms which include but not limited to gels, foams, suppositories, creams, lotions, tablets, pessaries, lubricants, and the like. Any formulation which allows the delivery of Ac-B in a quantity sufficient to neutralize HIV, inactivate spermatozoa.

The formulations may further include other ingredients which are well known to those of skill in the art, including but not limited to stabilizers, colorants, preservatives, perfumes, gelling agents, antioxidants, other active ingredients and the like. The composition of matter of the present invention may contain pure Ac-B or equivalent amount in an Ac-B enriched fraction of the seed extract of *Acacia auriculiformis*.

The composition of matter of the present invention may also be used in conjunction with other contraceptive devices. Examples include but not limited to: addition to condoms or diaphragms to enhance their activity, or to imbibe a cervico-vaginal sponge that would act both as a mechanical and chemical barrier against HIV infection and sperm penetration into upper reproductive tract.

The present invention further provides a method of contraception in female mammals, which involves placing a contraceptively effective amount of Ac-B in the vaginal cavity of a female mammal. Those of skill in the art will recognize that a variety of means are known by which a compound may be delivered intravaginally, for example plunger-type applicators, pessaries, film, sprays, squeezable tubes, cervical rings, sponges and the like. All such means for intravaginal delivery are intended to be encompassed by the present invention.

The present invention also provides a method of topical application of Ac-B in any suitable formulation of any suitable form as protection against HIV-1 infection in organs, including vagina of mammalian female where contraception is not a primary objective and the spermicidal property of Ac-B is superfluous.

The present invention also provides a method of topical application of Ac-B in any suitable formulation of any suitable form as protection against HIV-1 infection in organs including mammalian rectum where prevention of HIV transmission is a primary objective.

Accordingly, the present invention provides the use of the compound Acaciaside-B [Ac-B], derivatives, analogues and pharmaceutically acceptable salts thereof and/or its mixture with other synthetic or natural substances as virucidal and spermicidal agents.

DETAILED DESCRIPTION OF THE INVENTION

Three isolates, (i) a mixture of two triterpenoid saponins (Acaciaside-A and Acaciaside-B), (ii) Acaciaside-B (Ac-B), and (iii) an Acaciaside-B enriched fraction (Ac-B-en-frn), were obtained from seeds of *Acacia auriculiformis*.

In the present invention, the compound Acaciaside-B and/or enriched fraction, its derivatives, analogues and pharmaceutically acceptable salts thereof and/or its mixture with other synthetic or natural substances are used as virucidal and spermicidal agents. The compound is isolated from the plant *Acacia auriculiformis*. The infectivity of HIV and motility of spermatozoa are inhibited simultaneously by the said compound. Ac-B and/or enriched fraction is utilized for the preparation of prophylactic formulations useful against HIV and as spermicidal agent.

In an embodiment, the virus is preferably human immunodeficiency virus [HIV], but may also include other retroviruses.

In another embodiment, the compound Ac-B is administered with a carrier in a water soluble form.

In another embodiment, the compound is administered via the vaginal or rectal route.

In yet another embodiment, the administrable form for the compound/s is selected from the group consisting of lubricated condoms, jelly-filled plunger-type applicators, pessaries, films, foams, squeezable tubes, cervical rings, sponges and the like.

In a further embodiment, the carriers are selected from the group consisting of proteins, carbohydrates, sugars, talc, cellulose, inorganic salts, starch-gelatin paste and pharmaceutically acceptable excipients.

In another embodiment, the MEC of the pure Ac-B is in the range of 0.5 to 2.5 microgram per ml for inactivation of HIV in vitro.

In yet another embodiment, the MEC of the pure Ac-B is in the range of 60 to 125 microgram per ml for spermicidal activity in vitro.

In another embodiment, the $EC_{50}$ of Ac-B is 22 microgram per ml for spermicidal activity in vitro for human sperm.

The said compound/s is not likely to affect the vaginal niche of *Lactobacillus* as it does not affect bacterial growth in culture up to a concentration of 500 milligram per ml.

The present invention also provides a pharmaceutical composition useful as a virucidal as well as a spermicidal agent comprising of therapeutically effective amount of the compound Ac-B, derivatives, analogues and pharmaceutically acceptable salts thereof along with pharmaceutically acceptable excipients.

In an embodiment, the carriers are selected from the group consisting of proteins, carbohydrates, sugars, talc, cellulose, inorganic salts, starch-gelatin paste and pharmaceutically acceptable excipients.

The present invention further provides a method for simultaneous prevention of HIV infection and unwanted pregnancy in a subject, comprising administering a therapeutically effective amount of the compound Ac-B, derivatives, analogues and pharmaceutically acceptable salts thereof optionally along with pharmaceutically acceptable excipients, to a subject in need thereof.

In an embodiment, the subject is human.

In another embodiment, the compound Ac-B is administered with a carrier in a water soluble form.

In another embodiment, the compound is administered via the vaginal route.

In yet another embodiment, the administrable form for the compound is selected from the group consisting of lubricated condoms, jelly-filled plunger-type applicators, pessaries, films, foams, squeezable tubes, cervical rings, sponges and the like.

The Tree, *Acacia auriculiformis*
Taxonomy:
Name: *Acacia auriculiformis* A. Cunningham ex Benth,
Family—Fabaceae;
Common name: Auri, Darwin black wattle, Earleaf Acacia, Papuan wattle, etc
Habitat:

*Acacia auriculiformis* is planted either as road side tree or may grow in the wild. Quickly reaching a height of 40 feet and a spread of 25 feet, Earleaf Acacia becomes a loose, rounded, evergreen, open shade tree (FIG. 1). It is often planted for its abundance of small, beautiful, bright yellow flowers and fast growth. The flattened, curved branchlets, which look like leaves, are joined by twisted, brown, ear-shaped seed pods. Growing 6 to 8 feet per year, Earleaf Acacia quickly grows into a medium-sized shade tree. This makes it a popular tree; however, it has brittle wood and weak branch crotches, and the tree can be badly damaged during wind storms. Prune branches so there is a wide angle of attachment to help them from splitting from the tree. Also be sure to keep the major branches pruned back so they stay less than half the diameter of the trunk. These technique might increase the longevity of existing trees.

Description:

The tree: Height: 35 to 40 feet; Spread: 25 to 35 feet; Crown uniformity: irregular outline or silhouette; Crown shape: round; Crown density: moderate; Growth rate: fast; Texture: medium; Trunk and Branches: droop as the tree grows, and will require pruning for vehicular or pedestrian clearance beneath the canopy; not particularly showy; should be grown with a single leader; no thorns Pruning requirement: requires pruning to develop strong structure; Light requirement: tree grows in full sun; Soil tolerances: clay; loam; sand; acidic; occasionally wet; alkaline; well-drained; Drought tolerance: high.

Foliage: The seedlings bear normal compound leaves. As these leaves become mature, the leaflets drop off and the petioles become flattened and leaf-like. These flattened petioles are called phyllodes and appears as simple leaves. Leaf arrangement: alternate; Leaf margin: entire; Leaf shape: linear; Leaf venation: parallel; Leaf type and persistence: broadleaf evergreen; evergreen; Leaf blade length: 4 to 8 inches.

Flower: Arranged on twig tips in panicle type of inflorescence; color: yellow; Flower characteristics: showy; spring flowering.

Fruit: Fruit shape: irregular; Fruit length: 1 to 3 inches; Fruit covering: dry or hard; Fruit color: green when young and brown at ripening.

Isolation and Identification of Saponins:

The air-dried and powdered seeds of *A. auriculiformis* were extracted with methanol. The combined methanolic extracts were evaporated to dryness, dissolved in water and partitioned between chloroform and n-butanol. The butanol fraction was chromatographed over silica gel eluting with solvent chloroform, chloroform-methanol (4:1), chloroform-methanol (7:3) and chloroform-methanol (1:1). The combined chloroform-methanol (7:3 and 1:1) fraction was rechromatographed to yield TLC homogeneous saponins. HPLC analysis of this glycoside fraction showed to be a mixture of two compounds. Preparative HPLC of this mixture with the help of reverse phase C-18 Bondapack column with solvent system methanol-water (7:30) afforded Acaciaside-A and Acaciaside-B.

Yield: From 1 kg seeds about 190 g methanolic extract was available which on further elution (a) with n-Butanol yielded 48 g of a mixture of which 5.84% was Acaciaside-A and 11.93% was Acaciaside-B; (b) with water yielding an aqueous fraction of which 38.11% was Acaciaside-B. This fraction was termed as B-enriched fraction (Ac-B-en-frn). Pure compounds were separated from the butanolic aqueous fraction. The elution of the methanolic extract with ethyl acetate yielded about 15 g of a product which did not possess any spermicidal property.

The chemicals used for preparation of reagents were of analytical grade and purchased from Sigma Chemical Co (St Louis, Mo., USA). Purified water (Milli-Q Biocel System, Millipore Corporation) was used for experiments. Disposable plastic wares were purchased from M/s. Tarsons (India). Working spermatozoa suspension were made in glass tubes containing Briggers, Whitten, and Whittengham's medium (BWW). The serial dilutions of (a) mixture of Ac-A and Ac-B, (b) Ac-B, and (c) the Ac-B-enriched fraction, were prepared in BWW medium, in concentrations, ranging from 10 µg/ml to 500 µg/ml, at a 100 or 10 µg apart. The final concentration was determined with more close dilutions (2.5 µg apart). The positive control (Nonoxynol-9) solutions were also prepared in a similar manner. Sterilized K-Y jelly (Johnson & Johnson Ltd, India) was used as vehicle as well as placebo for in vivo testing.

Animals and Housing:

The laboratory animals used in the assay of different parameters were obtained and kept in the institutional Animal House with 22-24 degree C. room temperature, 55-60 percent relative humidity and 12:12 hour circadian rhythm. The rodents were kept in polypropylene cages with stainless steel grill-top and rabbits were kept in stainless steel cages of appropriate size. The animals were allowed sufficient space and other provisions in their cages as per recommendation of the Committee for the Purpose of Control and Supervision of Experimentation on Animals (CPCSEA), Ministry of Social Justice and Empowerment, Govt. of India. Balanced diet and purified drinking water were provided ad libitum to all animals.

In general, tests were performed with Sprague-Dawley rats, Balb/C mice and New Zealand Rabbits. The vaginal cytology of the female rats was monitored daily for at least two weeks via saline lavage to identify female rats with regular 4-5 day estrous cycle.

Human Sample:

Human semen samples and normal cervical mucus of ovulatory phase were collected from an infertility clinic, Institute of Reproductive Medicine, Kolkata, after their utilization of required volume for diagnostic purposes, and with due approval.

Medium:

The composition of BWW medium used in the tests was: 95 mM NaCl, 44 μM sodium lactate, 25 mM NaHCO$_3$, 20 mM Hepes, 5.6 mM D-glucose, 4.6 mM KCl, 1.7 mM CaCl$_2$, 1.2 mM KH$_2$PO$_4$, 1.2 mM MgSO$_4$, 0.27 mM sodium pyruvate, 0.3% (w/v) BSA, 5 I.U./ml penicillin, 5 μg/ml streptomycin, pH 7.4.

Collection and Preparation of Spermatozoa Suspension:

Sexually mature male mice and rats were autopsied following euthanasia by an overdose of Ketamin (≥200 mg/kg body weight; injected i.p.) and their cauda epididymis were excised. Working suspension of animal spermatozoa was prepared with the exudates obtained after careful pricking of the cauda epididymis with an injection needle (18 G) and the exudates were collected in a conical centrifuge tube.

The exudates/liquefied human semen samples were suspended in BWW medium (pre equilibrated at 37 degree C.). The spermatozoa with forward motility were separated from immotile or sluggishly motile cells by the swim-up technique and were allowed to disperse evenly within a CO$_2$ incubator at 37 degree C. At least five aliquots from each sample was used to prepare the working spermatozoa suspension. The swim up procedure was as follows:

Pre equilibrated BWW medium (1.25 ml) was gently layered over cauda-exudates or liquefied human semen (1 ml) in a sterile 15 ml conical-based centrifuge tube. The tube was inclined at an angle of 45 degree and incubated for 1 hour at 37 degree C. in a CO$_2$-incubator. It was then gently returned to the upright position and the uppermost 1 ml medium with a turbid appearance was removed. This aliquot of motile cells was pooled from each set, then diluted with same volumes of pre equilibrated BWW medium, centrifuged at 500 g for 5 minutes and finally resuspended in 1 ml pre equilibrated BWW medium to obtain a working suspension. The sperm cells were counted in a Makler chamber (Zygotec Systems, Springfield, M A, USA) and finally a working spermatozoa suspension having concentration of 25 to 30×10$^6$ cells/ml was prepared.

Test for Spermicidal Activity (In Vitro):

For in vitro assay of spermicidal effect, sperms collected from proven male rats and mice, and motile spermatozoa from liquefied human semen were used.

Experiment:

The assay was done following the Sander & Cramer assay method. Two hundred micro liter (200 microliters) of working spermatozoa suspension was added to 1 ml solution of test material in BWW medium and mixed on a light vortex for 10 seconds. A wet mount was immediately prepared on a clean microscopy glass slide and examined (at ×100) under a phase contrast microscope (Leitz, Biomed). The weakest concentration that immobilized all spermatozoa within 20 seconds of mixing was recorded as MEC. At least five fields were examined for each wet mount preparation. The observation was repeated with five individual spermatozoa suspension for each concentration of test compound solution. For negative control, saponin solutions were replaced by equal volume of BWW medium, while Nonoxynol 9 was used as positive control.

Result:

The results of Sander and Cramer Test are summarized in following Table 1.

The in vitro studies showed that the mixture (Tg), Ac-B and the Ac-B-en-frn, all have spermicidal property. With an increase in the concentration of the isolates, there was a dose-dependent increase in the immobilization of sperm. The MEC for each compound was different from others. Pure Ac-B was found to be the most potent. It induced 100% immobilization at 125 microgram per ml for human spermatozoa as compared to >350 microgram per ml for Nonoxynol 9 and 170 (±5) for Ac-B-en-frn.

TABLE 1

Comparison of MEC as per Sander and Cramer Test (in microgram per ml)

| Species | Mixture (Tg) of Ac-A & Ac-B | Ac-B | Ac-B-en-frn | Nonoxynol 9 |
|---|---|---|---|---|
| Human (N = 5) | 350 (±10) | 125 (±7) | 170 (±5) | >350 |
| Rat (N = 10) | 300 (±10) | 60 (±2) | 80 (±5) | 350 (±10) |
| Mouse (N = 10) | 270 (±20) | 60 (±2) | 80 (±5) | 350 (±10) |

Assessment of Contraceptive Efficacy of Ac-B (In Vivo):

The foregoing results of in vitro tests attest to the spermicidal potential of Ac-B. However, the overall objective was the use of developed spermicides as an effective molecule in vaginal contraceptives. It was therefore important to assess how effective the in vitro spermicidal property of Ac-B is in inducing contraceptive effects in vivo. Keeping these objective in view, an evaluation was made on the effects of Ac-B, administered in vivo on the establishment of pregnancy in rat and rabbit.

Experiment 1: Intra Uterine Application and IUI in Rat:

Female cycling rats weighing 180-200 g were obtained from the institutional Animal House. The duplex nature of the rat uterus with separate cervical canal helped us to organize both control and experimental sets in the same animal with exposure to identical physiological milieu.

On the day of pro-estrous, both horns of the uterus were exposed by mid-ventral incision of the abdomen under light anesthesia following intra peritoneal injection of Ketamin at a concentration of 100 mg/kg body weight, supported by inhalation of anesthetic-ether, during 17.00-17.30 hours of the day. IUI was performed by injecting 50 microliters of sperm suspensions with varied concentration (25-30, 40-50, and 50-55 million sperms/ml) through a 24 G needle fitted onto a tuberculin syringe in the cervical end of the uterine lumen of each horn. The muscle in the injection site was held tightly for a while to prevent leakage through the puncture. Prior to IUI, each rat received a injection of 1.75 mg Ac-B in 50 microliters BWW medium in the left horn and simple BWW medium in the right horn. The opened abdominal muscle and skin layers were properly sutured by suturing silk thread. The outer most skin layers were further fixed by metal clips. The wound was properly cleaned with antiseptic lotions. Each operated animal was housed individually in fresh cage for collection and counting of unfertilized oocytes, two celled embryos, and fragmented bodies. After 40 to 48 hours of IUI, each animal was killed by euthanasia. The abdomen was opened and each of the fallopian tubes was collected carefully. The content of each tube was flushed out by introducing BWW medium into each tube with the help of a 30 G hypodermic needle in a watch glass. The flushed out lavage was examined under an inverted phase contrast microscope (Leitz, Labovert, ×100) to score the number of recovered fertilized/unfertilized eggs from individual fallopian tube. The results obtained are illustrated in Table 2.

TABLE 2

Fertilization outcome in rats following IUI with prior IU administration of Ac-B

| Sperm count | Rate of fertilization as observed after flushing (38-40 hours after IUI) | | | | | |
|---|---|---|---|---|---|---|
| (million/ml) | Treated horn (Ac-B in BWW) | | | Control horn (BWW medium) | | |
| used for IUI | Fertilized | Unfertilized | Total | Fertilized | Unfertilized | Total |
| 25-30 (N = 3) | 0 (0%) | 17 (100%) | 17 | 10 (62.25%) | 6 (37.5%) | 16 |
| 40-50 (N = 4) | 0 (%) | 19 (100%) | 19 | 12 (80%) | 3 (20%) | 15 |
| 50-55 (N = 4) | 3 (18%) | 13 (82%) | 16 | 17 (85%) | 3 (15%) | 20 |

Experiment 2: Contraceptive Efficacy of Ac-B Following Intravaginal Application in Rabbits Healthy virgin, nulliparous female rabbits were primed with PMSG (200 i.u.; i.p.; 96 hrs prior to testing) to induce ovulation. Serial dilutions (2.5 mg/ml, 10 mg/ml, 25 mg/ml and 50 mg/ml) of Ac-B in KY-jelly was prepared to be used as test solutions and only KY-jelly was used for control group. Two ml of test/control solution was introduced 6-8 cm deep into the vagina of each rabbit with by the syringe with gavaging needle. The animal was held in supine position for about five minutes and then hand-mated by the selected proven bucks. The buck was allowed one-time mating. To ensure ovulation 100 i.u. of hCG was administered through the marginal ear vein of each participating doe. The vaginal lavage of the mated doe was examined under a microscope. The presence of spermatozoa in the lavage was considered as confirmed mating. The mated does were kept in separate cages to complete their gestation period and the number of delivered pups was recorded. The mean value of the pups was calculated to determine the contraceptive potential.

The results of intravaginal application of Ac-B have been summarized in Table 3. The result of each test group was compared with corresponding control group.

TABLE 3

Pregnancy outcome in rabbits following intra-vaginal application of Ac-B

| | | treated (n = 5) | | | |
|---|---|---|---|---|---|
| | | Concentration of Acaciaside-B in K-Y jelly | | | |
| statistical parameters | Control (n = 5) | 2.5 mg/ml | 10 mg/ml | 25 mg/ml | 50 mg/ml |
| Mean numbers of pups delivered | 3.6 | 3.4 | 2.2 | 0.2 | 0.0 |
| SD | ±1.14 | ±1.14 | ±0.84 | ±0.45 | 0.0 |
| P value | | NS | P = 0.058 | P = 0.0003 | |

P = as compared with control,
NS = Non significant
N = number of rabbits,
* = as compared with control,
P < 0.05 is significant Investigations on Mechanism of Spermicidal Effect Spermicidal potential of Ac-B in vitro has been tested in rats, mice and humans, while in vivo contraceptive efficacy has been conducted in rabbits. Subsequent investigations pertaining to mechanism of spermicidal action and related studies have been performed using human spermatozoa only.

1. Motility Revival Tests:

Experiment A:

Human spermatozoa, treated with Ac-B at MEC and BWW control set were washed twice in pre-equilibrated BWW medium, re-suspended in fresh BWW medium and again incubated in a $CO_2$-incubator at 37 degree C. for 30-60 minutes. At the end of the incubation, wet-preparation of spermatozoa was made from each set on a glass slide. The preparation was examined under a phase contrast microscope (at ×400) to note reversal of motility in 10 fields-of-view.

Experiment B:

A modified Kremer-Test was used for assessment of cervical mucus penetrating capacity of treated sperm.

A drop of human mid-cycle cervical mucus was placed on a slide and flattened by a cover slip (22 mm×22 mm). A drop of human sperm suspension treated with the test compounds (at MEC) was deposited at the side of the cover slip and in contact with the edge, the sperm suspension moved in under the cover slip by capillary force and a clear interface was obtained between the sperm suspension and the cervical mucus. The slide preparation was placed within a $CO_2$ incubator at 37 degree C. for 30 minutes. Suitable control sets were prepared side by side. Each preparation was examined under a phase contrast microscope to observe the entry of spermatozoa into the cervical mucus zone.

Experiment C:

Penetrak Test (bovine cervical mucus penetration test).

The bovine cervical mucus penetration test was performed using the Penetrak kit (Serono Diagnostics, Allentown, Pa.).

Working suspension of human spermatozoa, prepared as above was treated in vitro with Ac-B at MEC, washed and resuspended in pre-equilibrated BWW medium. For the negative control set, same treatment was given to the sperms in BWW medium. Flat-capillary tubes filled with periovulatory mid-cycle bovine cervical mucus, in duplicate, were thawed at room temperature for 30 minutes and snapped at the red score mark above the mucus meniscus. The cut end was placed in tube containing treated/control washed sperm suspension and placed inside a $CO_2$ incubator for 1 hour. The capillary tubes were then taken out, cleaned to remove superficially attached sperms, placed on a calibrated slide and examined by phase contrast microscopy (at ×400). The vanguard sperm was located and the distance (in mm) covered by it was measured to score the penetrating capacity of a sperm of the test sets.

Results:

Experiment A:

At the end of the incubation at 37 degree C., no sign for revival of motility was noted in the Ac-B-treated spermatozoa.

Experiment B:

At the interface, finger like projections of sperm suspension/s those penetrating into the cervical mucus was noted within a short period. In the BWW control set, a large number of spermatozoa penetrated the phalangeal canal before entering the mucus. Once in the cervical mucus, the motile spermatozoa swarmed at random. In case of Ac-B-treated spermatozoa, the sperms entered in the phalanges by capillary action and showed a Brownian movement but none of them crossed into the interface.

Experiment C: Penetrak Test:

In the BWW control set, vanguard sperm was noted at a distance of about 27(±3) mm but in Ac-B-treated set, it was found that the capillary was devoid of sperm inside the mucus column indicating irreversible loss of motility caused by exposure of sperms to Ac-B.

2. Assessment of Plasma Membrane Integrity of Ac-B Treated Human SPERMatozoa:

The foregoing results clearly demonstrated that Ac-B induces irreversible immobilization of the sperms which seems to be attributed to spermicidal effects of the molecules. The inventors therefore employed a battery of tests to assess the mode of execution of the spermicidal effects of Ac-B.

A functional membrane is important for the enzyme reactions necessary for a sperm to penetrate into the egg during fertilization. This is indicated by transport of selected molecules through the membrane. If trans-membrane transport does not occur or the membrane loses its selective permeability, it can be assumed that the membrane is chemically inactive or physically damaged and it would be unable to participate in the fertilization process.

A sperm with intact and functional plasma membrane, when placed in a hypo-osmotic environment will swell by influx of water. Its cell volume increases and become turgid (HOS test) with curling of tails into different shapes (HOS positive cells) but if the plasma membrane loses its integrity no such curling occurs (HOS negative cells). Again, the loss of this selectivity indicates that the cell is dead. The live-dead status of a treated sperm can be assessed by a dual fluorescent staining technique (live/dead staining). The mechanism of spermicidal activity of test agent was assessed here by hypo-osmotic swelling test (HOS Test), supra-vital staining and electron microscopy.

A. Live/Dead Staining of Treated Sperm

Live/dead staining kit (Invitrogen: Paisley, UK), using SYBR-14 in combination with propidium iodide (PI) was used for the purpose.

The SYBR-14 was prepared in anhydrous methyl sulfoxide (DMSO) at a concentration of 1 mg/ml. A working solution of SYBR-14 diluted 1:10 with DMSO was used for staining the sperm. The PI was dissolved in Tyrode's salt solution at 2 mg/ml.

The human sperm samples, pre-treated without (control) or with Ac-B (experimental) and Nonoxynol 9 (positive control) were incubated for 15 min at 36 degree C. before examination. When this stain combination was excited at 488 nm, the nucleus of the SYBR-14-stained normal sperm fluoresced bright green while the dead sperm nuclei exhibited red fluorescence (PI). The fluorescent staining of sperm was monitored and photographed with a Zeiss Axiophot epifluorescent microscope (Carl Zeiss Inc., Thornwood, N.Y.) equipped with a fluorescein isothiocyanate filter set (Zeiss #487909).

The results are summarized in Table 4 below.

B. Hypo-Osmotic Swelling (HOS) Test

A hypotonic solution was prepared by dissolving 0.735 g sodium citrate dehydrate and 1.351 g fructose in 100 ml distilled water (Milli Q). Aliquots of this solution kept frozen in −20 degree C. and thawed before use. For the test, 200 microliters of working suspension of rat spermatozoa was treated with one ml of Ac-B solution (at MEC) or BWW (as control) for 20 seconds followed by washing with BWW medium and centrifugation at 1000 rpm for 5 min. Finally the sperm pellet was resuspended in 0.1 ml BWW medium. One ml of prewarmed (37 degree C.) HOS solution was added to the suspension and incubated for one hour at 37 degree C. The incubated sperms were examined under a phase contrast microscope at ×400 magnification to observe the curling of tails. Two hundred spermatozoa were examined for each sample.

Results:

The result of HOS test also agreed well with the live/dead staining findings over ≥85% control spermatozoa responded to hypo-osmotic swelling and curling of the tail while Ac-B treated spermatozoa showed no HOS reactivity (Table-4).

TABLE 4

Effects of live/dead staining and hypo-osmotic swelling

| | Percentage of dead spermatozoa or Response to HOS | |
|---|---|---|
| | Ac-B | BWW |
| Live/dead staining | 92 (±5)% | 10 (±5)% |
| Hypo-osmotic Swelling Test (HOS) | 0% (HOS+) | 85% (HOS+) |

C. Assessment of Plausible Biochemical Mechanism

The biochemical change that may initiate the spermicidal activity is likely to be peroxidation of lipid layer of the cell membrane. The effect of conjugated unsaturated diene system of the Ac-B might be involved in producing the damaging effect, probably by consequential formation of free radicals that induce membrane damage through peroxidation of lipid. Lipid peroxidation triggers the loss of membrane integrity, causing increased cell permeability, enzyme inactivation, and structural damage to DNA, and ultimately cell death Accordingly, Ac-B probably generates free radicals that induce membrane damage through peroxidation of the polyunsaturated fatty acids (pFA), present in the phospholipids of spermatozoal membrane, resulting in the formation of soluble malondialdehyde (MDA). So the MDA concentration in suspension of treated sperm was assessed using the thiobarbituric acid (TBA) method.

Assessment of Membrane Lipid Peroxidation:

Membrane lipid peroxidation was estimated by the end point generation of malondialdehyde (MDA) determined by the thiobarbituric acid (TBA) test.

Suspension of human spermatozoa was prepared using the swim up technique, as described above. A series of dilutions (10, 20, 40, 60, 80, 100 and 120 microgram per ml) of Ac-B was prepared in BWW medium. From each test (Ac-B) solution, 800 microliters was taken out and mixed with 200 microliters of sperm suspension with a gentle vortex for 10 seconds. After 20 seconds of mixing, the treated spermatozoa were separated from the suspending medium by centrifugation. The pellet of washed spermatozoa was resuspended in physiological saline. A control set of untreated sperm was treated similarly. Membrane lipid peroxidation was estimated by the end point generation of malondialdehyde (MDA), determined by the thiobarbituric acid (TBA) test.

Briefly, diluted spermatozoa with or without treatment ($250 \times 10^6$ cells in 1 ml) were mixed with 1 ml of cold 20% (wt/vol) trichloroacetic acid (TCA) to precipitate protein. The precipitate was pelleted by centrifugation (2000 rpm for 10 minutes), and 1 ml of the supernatant was incubated with 1 ml of 0.67% (wt/vol) TBA in a boiling water bath at 100 degree C. for 30 minutes. After cooling, the absorbance was determined by a spectrophotometer (UNICAM PU 8610 Kinetics spectrophotometer; Philips, Holland) at 535 nm.

Results:

The spectrophotometric readings clearly demonstrated that there was an increase in the production of MDA (microgram per ml) along with an increase of concentration of the Ac-B. This observation extended support to the reported damaging effects of acaciasides on lipid molecules of the plasma membrane.

D. Electron Microscopy of Treated Sperm

For electron microscopy, the suspending medium was replaced with 0.1M phosphate buffer (pH 7.0). A concentrated untreated (control) and Ac-B-treated (experimental) human sperm suspension were mixed with 2% glutaraldehyde in phosphate buffer for fixation at 4 degree C. for 4 hours. After three successive washings in buffer at room temperature, post-fixation was done by 1% osmium tetroxide. Thirty minutes after post-fixation, the spermatozoa were quickly washed with phosphate buffer and end block staining was done by saturated urenyl acetate solution. Dehydration of the fixed spermatozoa was done in graded (50%, 70%, 90% and 100%) ethyl alcohol. A portion of each set of dehydrated sperms were embedded in spur and blocks were prepared for ultra-thin sectioning. Ultra-thin sections were prepared in LKB Ultramicrotome using a diamond knife. Finally the thin sections were stained with urenyl acetate and freshly prepared lead citrate. The stained sections were thoroughly examined under TECHNI G2 BIOTWEEN transmission electron microscope (at ×25000). The rest of the dehydrated sperm sets were prepared for examination under tescan scanning electron microscope.

Results:

In the control set all cells demonstrated the presence of intact plasma. The acrosomal cap was also found to be intact. But the saponin-treated sperms exhibited damaged plasma membrane of various degrees ranging from vesiculation, vacuolization to complete disintegration and their acrosomal cap was most severely damaged.

Assessment of Microbicidal Potential a. Effect on In Vitro Culture of *Lactobacillus acidophilus*

The media for culture of bacteria purchased from HI-MEDIA, India and spores of *Lactobacillus acidophilus* were obtained from pharmaceutical capsule marketed by Infer (India) Limited.

Sterile, molten (45-50 degree C.) Lactobacilli MRS agar was poured into sterile Petri dishes with (a) 1, 10, 100, 200, 500 mg of Ac-B (Experimental) and (b) without Ac-B (Control). The plates were placed within an incubator having 37 degree C. inside temperature and 5% $CO_2$ in air for 72 hours. The number of colonies and their individual size were compared.

The size of colonies grown in the presence of Ac-B was comparable to that of control. Comparative evaluation demonstrated that at least up to 500 milligram per ml dose level Ac-B does not affect the growth of *Lactobacillus acidophilus* cultured in vitro.

The results indicated that Ac-B possibly would not have any impact on vaginal population of *L. acidophilus* so as to disturb the vaginal ecology.

B. Effect on In Vitro Culture of *Candida albicans* for 24 Hours

*Candida albicans* spores were grown in vitro on Potato dextrose [PD] agar plates without (control) and with Ac-B at a concentration of 125 microgram per ml. It was observed that there was no significant difference between the number of colonies grown in the presence or absence of Ac-B. However, the sizes of the individual colonies were comparatively smaller in the Ac-B exposed group. This indicated that Ac-B might have a possible anti-microbial beneficial side effect on topical use.

Screening of Mutagenic Potential of Ac-B

Ac-B was examined for its ability to produce mutations/revert mutations in a bacterial reverse mutation assay using amino acid-requiring strain of *Salmonella typhimurium* (*S. typhimurium*) TA100 and the result was compared with a known mutagen (Na-azide). A commercial kit (The MUTA-CHROMOPLATE) from M/s Environmental Biodetection Products Inc. Ontario, Canada, was used. Suspensions of bacterial cells were exposed to the test substance in the presence and in the absence of an exogenous metabolic activation system. After 5 days of incubation, revertant colonies were detected by the change of colour from blue to yellow on solvent control plates. All yellow, partially yellow or turbid wells were scored as positive, while all purple wells were scored as negative. Number of positive wells for each plate was recorded, their number was counted and compared to that of spontaneous revertant colonies. The "Background" (i.e. no test material added) plate was used as reference for the level of spontaneous or background mutation of the assay organism. The statistical difference was determined using a table provided with the kit. It was observed that at least up to 10 milligram per ml concentration, Ac-B showed no positive mutagenic effect.

Score of mutagenicity as per the set criteria of Muta-Chromoplate test kit. All yellow, partially yellow or turbid wells were scored as positive, all purple wells were scored as negative.

A. Blank (No. of '+' wells==0)
B. Background (No. of '+' wells==20)
C. '+'Control (Na-azide) (No. of '+' wells==74)
D. Acaciaside-B (No. of '+' wells==18)

The overall results showed that Ac-B is non-mutagenic.

Test for Anti-HIV Potential

1. Anti-HIV Screening in CEM-GFP Cells:

Human CD4+ T cell line CEM-GFP cells were infected with HIV-1 NL-4.3 virus pretreated without or with Ac-B at varying concentrations (1 hour at 37 degree C.) at a multiplicity of infection (MOI) of 0.01. The cells were then cultured in the presence or absence of Ac-B for up to 7 days post infection. Virus production was analyzed in the culture supernatant on day-7 post infection by p24 antigen capture ELISA Cells infected with untreated virus but subsequently cultured in the presence of Ac-B (0.1 to 2.5 microgram per ml) showed only partial inhibition of viral transmission. However, complete inhibition was observed when cells were infected with Ac-B treated virus and cultured in the presence of Ac-B at concentrations greater than or equal to 1.0 microgram per ml). This observation clearly indicated inhibition of HIV-1 replication in T cells under exposure to Ac-B.

TABLE 5

Percentage inhibition of hiv growth in CEM-GFP T cell line

| Ac-B Concentration (microgram per ml) | Pretreatment with Ac-B | Without Pretreatment |
|---|---|---|
| 0.1 | 70.5 | 0 |
| 0.2 | 77.8 | 0 |
| 0.25 | 92 | 0 |
| 0.5 | 90.6 | 36.1 |
| 1 | 99.73 | 60.5 |
| 1.5 | 100 | 100 |
| 2 | 100 | 100 |
| 2.5 | 100 | 100 |

B. Anti-HIV activity in P4 (Hela-CD4-LTRβ Gal) cells

P4 (Hela-CD4-LTR-β Gal) cells were infected with 0.05 MOI of NL4.3 virus pretreated without or with Ac-B at varying concentrations (1 hour at 37 degree C.) followed by incubation for 48 hours in the presence or absence of Ac-B at a concentration of 0.5 to 2.5 microgram per ml. Virus production was analyzed by ELISA of p24 antigen in the culture supernatant. Viral transmission in the transfected cells was evaluated by X-gal staining, in which an antiretroviral therapeutic drug, Azidothymidine (AZT) was used as positive control. There was no inhibition of viral transmission when the cells were infected with untreated virus and cultured in the presence of Ac-B. However, viral transmission was inhibited >95% when the cells were infected with Ac-B-treated virus, irrespective of whether subsequent culture was conducted in the presence or absence of Ac-B (greater than or equal to 1.5 microgram per ml).

As assessed by X-gal staining, anti-HIV activity offered by Ac-B at concentration 1.0 microgram per ml (0.005 micromoles) was comparable to or greater than that induced by AZT at 2 micromole concentration.

TABLE 6

Percentage inhibition of hiv growth in p4 cell line

| Ac-B Concentration (microgram per ml) | Pretreatment with Ac-B | Without Pretreatment |
|---|---|---|
| 0.5 | 76.53 | 0 |
| 1 | 95.86 | 0 |
| 2 | 96 | 0 |
| 2.5 | 95.53 | 0 |

CONCLUDING REMARKS

Though like most of the popularly used marketed spermicides (viz. Nonoxynol-9), Ac-B is a nonionic surfactant, it differs from N-9 in following respects:

Pure Ac-B is a natural compound of herbal origin having molecular size of about three fold bigger than the synthetic molecule of N-9. This characteristic feature may favour poor absorption through vaginal epithelium and entry into systemic circulation.

Its MEC for spermicidal action (125 microgram for human sperm) is much less than that of N-9 (MEC 200-500 microgram).

Ac-B has no adverse impact on *Lactobacillus* growth in culture and therefore is expected to have no adverse impact on vaginal ecology, while Nonoxynol-9 is known to damage vaginal microflora that renders the subject susceptible to opportunistic infections including HIV.

Finally, significant spermicidal as well as virucidal activities with apparently no possible mutagenic effects and adverse effects on vaginal ecology highlight the credential of Acaciaside-B as a prospective candidate molecule for future development of spermicidal microbicide, which is however, subject to proper evaluation of its safety margins.

EXAMPLES

The following examples are given by way of illustration of the present invention and therefore should not be construed to limit the present invention.

Example 1

Anti-HIV Screening in CEM-GFP Cells

Human CD4+ T cell line CEM-GFP cells were infected with HIV-1 NL-4.3 virus pretreated without or with Ac-B at varying concentrations (1 hour at 37° C.) at a multiplicity of infection (MOI) of 0.01. The cells were then cultured in the presence or absence of Ac-B for up to 7 days post infection. Virus production was analysed in the culture supernatant on day-7 post infection by p24 antigen capture ELISA (FIG. 1).

Cells infected with untreated virus but subsequently cultured in the presence of Ac-B (0.1-2.5 mcg/ml) showed only partial inhibition of viral transmission. However, complete inhibition was observed when cells were infected with Ac-B treated virus and cultured in the presence of Ac-B at concentrations (≥1.0 mcg/ml). This observation clearly indicates inhibition of HIV-1 replication in T cells under exposure to Ac-B (FIG. 2).

Example 2

Anti-HIV Activity in P4 (Hela-CD4-LTR-β Gal) Cells

P4 (Hela-CD4-LTR-β Gal) cells were infected with 0.05 MOI of NL4.3 virus pretreated without or with Ac-B at varying concentrations (1 hour at 37° C.) followed by incubation for 48 hours in the presence or absence of Ac-B (0.5-2.5 µg/ml). Virus production was analyzed by ELISA of p24 antigen in the culture supernatant (FIG. 1). Viral transmission in the transfected cells was evaluated by X-gal staining, in which an antiretroviral therapeutic drug, Azidothymidine (AZT) was used as positive control (FIG. 4). There was no inhibition of viral transmission when the cells were infected with untreated virus and cultured in the presence of Ac-B. However, viral transmission was inhibited >95% when the cells were infected with Ac-B-treated virus, irrespective of whether subsequent culture was conducted in the presence or absence of Ac-B (≥1.0 mcg/ml) (FIG. 3).

As assessed by X-gal staining, anti-HIV activity offered by Ac-B at concentration 1 µg/ml (0.005 µM) was comparable to or greater than that induced by AZT at 2 µM concentration. (FIG. 4).

Example 3

Spermicidal Activity In Vitro

As evaluated by Sander-Cramer test, Ac-B is spermicidal for human, mice, rats. The MECs, however, vary between the species: the lowest (60 µg/ml) for rats/mice and highest (125 µg/ml) for human sperm. Motility revival tests proved the loss of motility to be irreversible.

Example 4

Assessment of Sperm Viability and Plasma Membrane Integrity

Viability of Ac-B-treated human spermatozoa was evaluated using a dual fluorescent live/dead staining kit (Invitrogen; Paisley, UK) consisting of SYBR 14 and propidium iodide (PI). PI cannot penetrate living cells but can bind to and stain cellular DNA in damaged cells giving them red fluorescence. On completion of staining reaction, proportionate distribution of green (live) and red (dead) stained spermatozoa was recorded using dual emission filter for SYBR14 and propidium iodide. In the control set all sperms were stained green but the Ac-B-treated spermatozoa (125 mcg/ml) were stained red. This observation clearly demonstrates that Ac-B exerts spermicidal but not spermatostatic effects.

Integrity of plasma membrane was tested by hypo-osmotic swelling (HOS) test. The curling of tails in the untreated (control) spermatozoa, caused by the turgidity due to imbibitions of water into the cell indicates intact integrity of plasma membrane around the cell. The absence of curling in the Ac-B treated spermatozoa indicates that the surrounding plasma membrane has lost its integrity.

The modus operandi of membrane damage involves increased lipid peroxidation of the plasma membrane leading to loss of integrity with consequent death of the exposed sperms. Increased lipid peroxidation was evident by Ac-B-induced dose-dependent increased generation of malondialdehyde (MDA). The electron microscopic study also confirms the membrane damaging effects of Ac-B. As observed in TEM, the damaging effect of Ac-B involves vesiculization/vacuolization of the plasma membrane leading to its disintegration. In the SEM of human sperm it has been observed that intact acrosomal cap and plasma membrane are present around the head and neck region of control sperms but the Ac-B-treated sperm shows mutilation of these regions.

Example 5

Effect on In Vitro Culture of *Lactobacillus acidophilus*

Comparative evaluation shows that at least up to 500 mg/ml dose level Ac-B does not affect the growth of *Lactobacillus acidophilus* cultured in vitro. The size of colonies grown in the presence of Ac-B is comparable to that of control.

This result indicates that Ac-B possibly would have no impact on vaginal population of *L. acidophilus* to disturb the vaginal ecology.

Example 6

Effect on In Vitro Culture of *Candida albicans* for 24 Hours

*Candida albicans* spores were grown in vitro on PD agar plates without (control) and with Ac-B at a concentration of 125 µg/ml. There was no significant difference between the number of colonies grown in the presence or absence of Ac-B. However, the sizes of the individual colonies were comparatively smaller in the Ac-B exposed group.

This indicates that Ac-B might have a possible anti-microbial beneficial side effect on topical use.

Example 7

Screening of Mutagenic Potential of Ac-B

Ac-B was examined for its ability to produce mutations/revert mutations in a bacterial reverse mutation assay using amino acid-requiring strain of *Salmonella typhimurium* (*S. typhimurium*) TA100 and the result was compared with a known mutagen (Na-azide). A commercial kit (The MUTA-CHROMOPLATE) from M/s Environmental Biodetection Products Inc. Ontario, Canada, was used. Suspensions of bacterial cells were exposed to the test substance in the presence and in the absence of an exogenous metabolic activation system. After 5 days of incubation, revertant colonies were detected by the change of color from blue to yellow on solvent control plates. All yellow, partially yellow or turbid wells were scored as positive, while all purple wells were scored as negative. Number of positive wells for each plate was recorded, their number was counted and compared to that of spontaneous revertant colonies. The "Background" (i.e. no test material added) plate was used as reference for the level of spontaneous or background mutation of the assay organism. The statistical difference was determined using a table provided with the kit.

At least up to 10 mg/ml concentration, Ac-B showed no positive mutagenic effect.

ADVANTAGES OF THE INVENTION

Acaciaside-B has an anti-HIV property and capable to prevent HIV infection at a dose level of greater than or equal to 1.0 microgram per ml in vitro, which is perhaps well within tolerable limits (Hemolytic index: 7 microgram per ml).

MEC of Ac-B is 125 micro g/ml for spermicidal activity on human sperm which is significantly lower than that of closest prior arts (MEC for N-9:200-500 microgram per ml Ac-B is non-mutagenic as tested in Ames Test.

Ac-B does not interfere with the growth of *Lactobacillus acidophilus* in laboratory culture, at least up to a concentration of 500 mg/ml.

Its molecular size is about three fold higher than N-9, which makes it likely to be absorbed weekly through vaginal route.

We claim:

1. A method for inhibiting the infectivity of a retrovirus which comprises administering to a subject in need thereof a retrovirucidally effective amount of a retrovirucidal composition wherein the virucide contained therein is the isolated compound Acaciaside-B and/or an Acaciaside-B-enriched fraction of mixture of Acaciaside-B and Acaciaside-A wherein the ratio of Acaciaside-B to Acaciaside-A exceeds 2.1:1 or a pharmaceutically acceptable salts thereof.

2. The method according to claim 1, wherein the compound is isolated from the plant *Acacia auriculiformis*.

3. The method according to claim 1, wherein Ac-B and/or enriched fraction is administered prophylactically against HIV and as spermicidal agent.

4. The method according to claim 1, wherein the virus is human immunodeficiency virus.

5. The method according to claim 1, wherein the compound Ac-B is administered with a carrier in a water soluble form.

6. The method according to claim 1, wherein the compound is administered via the vaginal or rectal route.

7. The method according to claim 1, wherein the compound/s is administered in a form selected from the group consisting of lubricated condoms, jelly-filled plunger-type applicators, pessaries, films, foams, squeezable tubes, cervical rings, and sponges.

8. The method according to claim 1, wherein the compound/s is administered in combination with a carrier are selected from the group consisting of proteins, carbohydrates, sugars, talc, cellulose, inorganic salts, starch-gelatin paste and pharmaceutically acceptable excipients.

9. The method according to claim 1, wherein the MEC of the Ac-B used is in the range of 0.5 to 2.5 microgram per ml for inactivation of HIV in vitro.

10. The method according to claim 1, wherein the MEC of the Ac-B is in the range of 60 to 125 microgram per ml for spermicidal activity in vitro.

11. The method according to claim 1, wherein the EC50 of Ac-B used is 22 microgram per ml for spermicidal activity in vitro for human sperm.

12. A method according to claim 1 wherein the virucide contained in said retrovirucidal composition is isolated compound Acaciaside-B.

13. A virucidal method which comprises administering to a subject infected with a retro virus a and in need of a treatment therefor a virucidally effective amount of a composition wherein the virucide is the compound Acaciaside-B and/or enriched fraction wherein the ratio of Acaciaside-B to Acaciaside-A exceeds 2.1:1, and pharmaceutically acceptable salts thereof and/or its mixture with other synthetic or natural substances.

14. The method according to claim 13, wherein the compound is isolated from the plant *Acacia auriculiformis*.

15. The method according to claim 13, wherein the virus is human immunodeficiency virus.

16. The method according to claim 13, wherein the compound Ac-B is administered with a carrier in a water soluble form.

17. The method according to claim 13, wherein the compound is administered via the vaginal route.

18. The method according to claim 13, wherein the administrable form for the compound is selected from the group consisting of lubricated condoms, jelly-filled plunger-type applicators, pessaries, films, foams, squeezable tubes, cervical rings, and sponges.

19. A virucidal method according to claim 13 wherein the virucide is isolated compound Acaciaside-B.

20. The virucidal and spermicidal method which comprises administering to a subject in need thereof a virucidally or spermicidally effective amount of a virucidal and/or spermicidal composition wherein the virucide and/or spermicide contained therein is the compound Acaciaside-B and/or an Acaciaside-B-enriched fraction of mixture of Acaciaside-B and Acaciaside-A wherein the ratio of Acaciaside-B to Acaciaside-A exceeds 2.1:1 or a pharmaceutically acceptable salt thereof wherein the infectivity of HIV and motility of spermatozoa are inhibited simultaneously by the said compound.

21. A method for simultaneous inhibition of HIV infection and reduction of conception in a subject, comprising administering a therapeutically effective amount of a composition having spermicidal and virucidal properties wherein the active spermicide and virucide in said composition is the isolated compound Ac-B, or a pharmaceutically acceptable salt thereof optionally along with pharmaceutically acceptable excipients, to a subject in need thereof.

22. The method according to claim 21, wherein the subject is human.

23. The method according to claim 21, wherein the compound Ac-B is administered with a carrier in a water soluble form.

24. The method according to claim 21, wherein the compound is administered via the vaginal route.

25. The method according to claim 21, wherein the administrable form for the compound is selected from the group consisting of lubricated condoms, jelly-filled plunger-type applicators, pessaries, films, foams, squeezable tubes, cervical rings, and sponges.

* * * * *